(12) United States Patent
Wilkins, Jr.

(10) Patent No.: US 8,492,443 B2
(45) Date of Patent: Jul. 23, 2013

(54) TREATMENT FOR HERPES SIMPLEX VIRUS AND OTHER INFECTIOUS DISEASES

(76) Inventor: Joe S. Wilkins, Jr., Navasota, TX (US)

( * ) Notice: Subject to any disclaimer, the term of this patent is extended or adjusted under 35 U.S.C. 154(b) by 1183 days.

(21) Appl. No.: 11/444,037

(22) Filed: May 31, 2006

(65) Prior Publication Data

US 2006/0217438 A1 Sep. 28, 2006

Related U.S. Application Data

(63) Continuation-in-part of application No. 10/615,589, filed on Jul. 8, 2003, now abandoned.

(60) Provisional application No. 60/394,333, filed on Jul. 8, 2002.

(51) Int. Cl.
*A01N 27/00* (2006.01)
*A61K 31/015* (2006.01)

(52) U.S. Cl.
USPC ............................................. 514/763

(58) Field of Classification Search
USPC ............................................. 514/763
See application file for complete search history.

(56) References Cited

U.S. PATENT DOCUMENTS

| | | | | |
|---|---|---|---|---|
| 3,023,144 A | * | 2/1962 | Greathouse et al. | 514/164 |
| 5,260,342 A | * | 11/1993 | Herman | 514/724 |
| 5,385,733 A | * | 1/1995 | Mankovitz | 424/771 |
| 5,894,019 A | * | 4/1999 | Hesse et al. | 424/484 |
| 5,900,416 A | * | 5/1999 | Markson | 424/728 |
| 6,077,862 A | * | 6/2000 | Camden | 514/388 |
| 6,419,936 B1 | * | 7/2002 | Schmoyer | 424/401 |
| 6,475,526 B1 | * | 11/2002 | Smith | 424/642 |
| 2002/0141959 A1 | * | 10/2002 | Peterson et al. | 424/70.12 |
| 2003/0104082 A1 | | 6/2003 | Squires | |

OTHER PUBLICATIONS

Bourne et al (Plant products as topical microbicide candidates: assessment of in vitro and in vivo activity against herpes simplex virus type 2, Antiviral Research, 42 (3) Jul. 1999, pp. 219-226).*
Sivropoulou et al (J. Agric. Food Chem. 1997, 45, 3197-3201).*
Herting and Drury (The Journal of Nutrition, 81(4) (1963) 335-342).*
Bourne et al (Antiviral Research, vol. 42, Iss 3, 1999, pp. 219-226).*
Australian office action for U.S. Appl. No. 10/615,589) (Jan. 7, 2008) (2 pages).

* cited by examiner

*Primary Examiner* — Benjamin Packard
(74) *Attorney, Agent, or Firm* — Laura G. Barrow

(57) ABSTRACT

Topical formulations and methods use are described herein for relieving symptoms created by herpes simplex, mouth ulcers, and yeast infections. The formulations comprise effective amounts of d-limonene.

7 Claims, No Drawings

TREATMENT FOR HERPES SIMPLEX VIRUS AND OTHER INFECTIOUS DISEASES

This application is a continuation-in-part of U.S. application Ser. No. 10/615,589, filed Jul. 8, 2003, now abandoned which claims the benefit of the filing of provisional application Ser. No. 60/394,333 filed Jul. 8, 2002. Ser. Nos. 10/615,589 and 60/394,333 are incorporated by reference herein in their entireties.

BACKGROUND OF THE INVENTION

The present invention relates to herpes virus, and more particularly, to medical treatments for herpes virus, mouth ulcers and other microbial infections.

Herpes simplex virus (HSV) commonly referred to as "herpes virus" or "herpes," is an infectious disease which has reached crisis proportions nationally with estimated numbers of infected people at 70%-80% of our population as reported by the American Social Health Association (ASHA) and growing annually by 500,000 people or more. There are two common types of herpes: herpes simplex virus 1 (HSV 1) and herpes simplex virus 2 (HSV 2).

Herpes enters the human body through minuscule breaks in the epidermal tissue usually by contact with an infected host and is marked by eruption of one or more vesicles, usually in groups, following an incubation period of approximately four to ten days. Typically the course of the infectious outbreak initiates with the prodromal stage; advancing to vesicular eruption; followed by: ulceration; coalescing; resolution; and the latency period. The outbreak can last for several weeks and on average lasts two-three weeks. In some immune compromised individuals the outbreak can last for months. The vesicles can appear anywhere on the skin or mucosa, typically appearing on the lips as cold sores, glands, oral mucosa, conjunctiva and cornea, genitalia, anal mucosa and perianal tissue.

Herpes symptoms include: inguinal swelling, pain, fever, malaise, headaches, muscle aches, and swollen glands. Some individuals with trigeminal nerve affected oral herpes, have excruciating facial pain, difficulty swallowing, eating and facial swelling. Individuals with the sacral nerve affected have severe upper leg pain, swelling, and great difficulty walking.

Herpes simplex virus (HSV) infection is recrudescent, residing in the nerve ganglia, and then recurring due to some, as yet unknown, stimulus. Recurrent herpetic infections can be precipitated by almost anything, including: overexposure to sunlight; nutritional deficiencies; stress, menstruation; immunosuppression; certain foods; drugs; febrile illness; etc. Recently herpes virus was isolated from cardiac tissue.

HSV 1 and HSV 2 infections pose very serious health threats often causing: blindness; increased cancer risk of the cervix; aseptic meningitis and encephalitis; neonatal deaths; viremia; etc. The devastating effects of this disease go well beyond the medical scope of human suffering; HSV is responsible for serious psychological and emotional distress as well as substantial economic loss to the nation and the world.

Various treatments for herpes have been proposed and have included topical application of such agents as povodone-iodine, idoxuridine, trifluorothymidine, or acyclovir. Such treatments have met with varying degrees of success. Most prior treatments have proven disappointing. Acyclovir, taken orally for systemic treatment of HSV, is somewhat effective. However, acyclovir is only successful in interrupting the replication of the virus and is used to treat infectious outbreak systemically. Nothing to date has proven really effective topically. Strains resistant to acyclovir have been reported. Individuals with Auto Immune Deficiency Syndrome (AIDS) are seriously immune-compromised and suffer especially debilitating outbreaks of HSV. Additionally, AIDS individuals may carry acyclovir resistant strains of HSV, which can make acyclovir ineffective for these individuals.

Despite the common occurrence of mouth ulcers and vast amounts of research, the cause of these irritating sores is still not completely understood. However, by far and away the most common cause is the infection of an injury in the mouth. These injuries can be cuts, abrasions or burns.

mouth ulcer affects the softer areas of the mouth, for example the tongue and cheeks. The surface layer of the skin is removed leading to the formation of the ulcer which usually appears circular with a yellow or white center and a raised red rim. It is because of the removal of the skin layer that nerve cells are exposed causing the associated pain.

Yeast infections can occur on numerous parts of the body. Some of the most common type of yeast infections are those which occur in the mouth or in vaginal area in women. Yeast infections are caused by an overgrowth of the *Candida albicans* fungus, which is a naturally occurring organism that normally lives quite harmlessly in your vagina, rectum, digestive tract and mouth. However, changes in a person's body can cause this fungus to proliferate, leading to a yeast infection. Yeast infection causes include the use of steroid containing medications or antibiotics, diabetics having elevated blood sugar levels, and the use of hormonal contraceptives.

SUMMARY OF THE INVENTION

The present invention is directed to dermatological, topical formulations, containing high purity d-limonene as an active ingredient in inhibiting the herpes virus, treating or preventing yeast infections (skin, oral cavity, or vaginal), and for relieving mouth ulcers.

DETAILED DESCRIPTION OF THE INVENTION

The present invention is directed to formulations containing high purity d-limonene as an active ingredient and methods of using these formulations for treating mouth ulcers, yeast infections (skin, vaginal, rectal, or oral cavity), or herpes simplex virus (HSV 1 & HSV 2) in humans, including topical dermatological preparations comprising d-limonene in a suitable carrier.

The present invention is directed to a composition, that when applied in the topical manner, rapidly relieves pain and heals lesions of herpes virus and mouth ulcers or canker sores as well as yeast infections. Advantageously, the improved treatment and composition are safe, inexpensive and effective. The present invention comprises a novel medical composition, formulation, antimicrobial compound and solution. The new antimicrobial medical treatment and microbicidal medicine are successful in treating primarily herpes simplex virus (HSV 1 & HSV 2) topically and may be useful in treating other herpes related microbial infections including, but not limited to: varicella zoster virus (herpes zoster) and cytomegalovirus.

Advantageously, the improved medical treatment and medicine of the present invention yielded unexpected, surprisingly good results. Initial topical, in vivo testing, demonstrated relief from pain in minutes and speedy total resolution of vesicular eruption in all individuals tested. When the inventive medical treatment and medicine are applied at the prodromal stage, the infection is interrupted and no further outbreak occurs. In vitro testing of the novel medical treatment and medicine demonstrated extremely surprising inhibitory effects on herpes virus. Desirably, the novel medicine is made from readily available, over the counter (OTC) chemicals or products and provides a safe comfortable, economical and user-friendly treatment.

This easy to use topical solution provides a coating upon application to either the prodromal tissue or the erythematous vesicular herpes lesion or mouth ulcer. Upon contact, there is a slight tingling effect. Within minutes of application, the pain of the infection resolves. Gradually, inguinal swelling subsides, fever, malaise, body aches, and nerve involvement subsides. Typically, within twenty-one hours all external symptoms and physical manifestations of infection are resolved and the vesicle is dried and resolved. A particularly surprising, beneficial effect provided by this inventive medicine, is that when it is applied at the first sign of outbreak, the prodromal stage, all symptoms and signs of further infectious outbreak is terminated. No eruptions appear or any further escalation of symptoms of the infection.

Desirably, the present medical composition includes a viral or microbial inhibitor, namely, d-limonene in the presence of a suitable carrier. The microbe inhibitor inhibits viral diseases, such as: herpes simplex virus 1 (HSV 1), herpes virus 2 (HSV 2), varicella zoster virus (herpes zoster) and the like including mouth ulcers. The present limonene containing compositions are also useful in treating or preventing yeast infections of the oral cavity, skin, rectum, or vagina. Limonene is a monocyclic monoterpene commonly found in the form of its d-isomer. D-limonene is one of the most common terpenes in nature, occurring in citrus fruits and a wide variety of other plant species. (Nat'l Toxicol Program Tech Rep Ser, 1990, Limonene, Monograph, 1999; 39:260-265). This flavoring agent, generally recognized as safe (GRAS) by the Food and Drug Administration, is widely used in fruit juice, soft drinks, baked goods, pudding and ice cream. Orange oil, naturally consisting of 90 to 96% d-limonene, is commercially available as a flavoring food agent.

The present treatment provides a novel method and process for use in treating the above infectious diseases by applying the microbial inhibitors on the microbial infected area and maintaining the microbe inhibitors on the infected area (region or surface) until the external symptoms and physical manifestations of the infection disappear, reside or resolve about the infected area. The composition can be applied by spraying, dabbing, swabbing, sponging, brushing, pouring, inserting a suppository (rectal or vaginal), dispensing, covering, douching, or heavily coating the medicine on the microbial infected areas, such as: oral mucosa, nasal mucosa, vaginal tissue, labial tissue, anal tissue, peri-anal tissue, lips, cutaneous tissue, sub-cutaneous tissue, ocular tissue, conjunctiva, and eyelids.

For the treatment of yeast infections, the composition can also be administered orally in a delayed-release formulation that will not disintegrate in the stomach, but rather is absorbed in the intestine for the treatment of yeast infections occurring vaginally, topically, rectally, and in the oral cavity. Suitable delayed release pharmaceutical formulation include incorporation of the d-limonene in a gel or other delayed-release formulation known by those of ordinary skill in the art.

Preferably, the present composition or microbial compound is a high purity, at least 98.5% by weight d-limonene combined and simultaneously or concurrently applied with a solvent or diluent to provide a microbicide medicinal solution.

Carriers are useful for mixing the constituents, keeping the constituents in solution, and providing an easy method of application to the affected area whether by spray, dropper, or applicator. While a liquid Vitamin E solvent is preferred for best results, in some circumstances it may be desirable to use other sterile aqueous carrier liquid or solid carriers, such as: glycerin, mineral oil, silica, cottonseed oil, coconut oil, vegetable oil, seed oil, fish oil, or animal oil, alcohol, talc, corn meal, beeswax, carnauba wax, beta carotene, garlic oil, camphor oil, soluble vitamins, soluble minerals, rape seed oil, nut oils, olive oil, liposomes, or other sterile carriers.

In certain embodiments, the formulations comprise an effective amount of d-limonene, preferably from about 10% to about 50% d-limonene mixed in a compatible vehicle, such as Vitamin E oil. A preferred formulation comprises only d-limonene and Vitamin E; however, it will be recognized by those of ordinary skill in the art at that other pharmaceutical bases conventionally used in the formulation of topical ointments, lotions, creams, solutions, shampoos, body soap, and the like may be employed. When d-limonene is combined with Vitamin E, the composition is heated to about 100° F. for a sufficient time during blending until the d-limonene is completely mixed therein (i.e. until a substantially homogenous mixture results). For best results, the improved formulation for the treatment for herpes, comprises by volume: 20% to 50% by volume of d-limonene, and 50% to 80% by volume of carrier such as Vitamin E, most preferably about 60% Vitamin E and about 40% d-limonene.

The inventive topical composition may be formulated in the aforementioned Vitamin E solution or various types of ointments, creams, lotions, substantially solid lip stick or lip balm compositions, suppositories, douches, troches, and the like, and then applied to the affected area on the patient's skin. When an effective amount of the inventive composition is applied to the affected area on the patient's skin, lips or mouth and mucosal area, healing effects are observed often within one day.

As described in more detail in the following examples, d-limonene, and in particular highly purified d-limonene (i.e. at least 98.5% purity), has been shown to be effective in killing or inhibiting the growth of a number of gram-positive and gram-negative bacteria.

The d-limonene may be purified by known distillation techniques, such as that described in U.S. Pat. No. 6,420,435, which is incorporated herein by reference in its entirety.

The inventive technology, treatment and medicine yield very attractive, unexpected, surprisingly good and consistent results. Tests show the composition of the present invention to be extremely useful to heal and control herpes outbreaks, viral shedding, extend the latency periods of the disease, and dramatically inhibit the virus, while being generally safe to the patient and the environment.

A more detailed explanation of the invention is provided in the following description and appended claims.

A herpes virus microbicide and treatment are provided to ease pain, heal lesions, resolve infectious outbreaks rapidly and inhibit herpes simplex virus 1 and 2 (HSV 1 & HSV 2). Desirably, the herpes microbicide and treatment completely inhibits herpes virus, as well as other infectious microbial diseases, and are safe and non-toxic to humans, animals, and the environment.

The composition of the present invention has demonstrated impressive activity against HSV 1 & 2, bacteria, viruses. The exact mechanism is unknown. When tested topically in vivo on HSV 1 & 2, it is somewhat effective in treating herpes simplex infectious outbreaks. When tested in vitro, it showed some inhibitory activity against HSV 1 & 2.

For preferred use, during any outbreak or physical manifestations of herpes and preferably at the first sign of the prodrome stage of tingling, itching, or irritation of herpes, the medical solution should be applied topically on the infected area. The affected (infected) area should be as dry as possible depending on location of outbreak. The method of topical application of medicine can be by: spraying, dabbing, dropper, or any such method as to coat the entire affected area. The coating of the solution (medicine) should be maintained until all external symptoms completely resolve, reapplying as needed anytime the coating diminishes, for instance, after showering. Anionic soaps and anionic detergents, and especially protein content soaps can be contraindicated. Preferably, the infected area should be washed, cleaned and dried prior to application of the medicine.

Clinical Pharmacology

When the d-limonene having a purity of at least 98.5% by weight was mixed with a liquid Vitamin E carrier, the results were unexpected and surprisingly good in resolving (treating) herpes virus and other infectious diseases and the effectiveness of the medicine (microbicide) dramatically increased. When the synergistic medicine was tested topically in vivo, the herpes simplex infections were immediately arrested. When the synergistic medicine was tested in vitro, there was a high level of inhibitory activity against HSV 1 & 2.

The medicine can be used in varying dilutions on: oral and nasal mucosa; vaginal tissue; labial tissue; anal and peri-anal tissue; penile tissue; cutaneous tissue; open subcutaneous tissue; and in higher dilutions on ocular infections. By varying the concentrations, the medicine may possibly be administered parenterally. The medicine may be contraindicated in vaginal or anal packs; in the ear canal; occlusive dressings; casts or ingestion and such use may produce irritation or chemical burns. It may not be advisable to use the medicine to treat anaerobic fungal infections, since some fungi may be resistant.

Example 1

In Vivo Testing

An initial, topical application, in vivo study was undertaken to evaluate the effects of the medical treatment and medicine of the present invention upon four human test subjects who had been tested positive for HSV 1 or 2. The subjects were treated topically with the medicine comprising d-limonene (40% pure by volume) in a Vitamin E oil solution (60% by volume). Application of the composition was made by wetting the affected area or vesicle with the solution by dabbing or using a dropper. An important aspect in this treatment was maintaining complete coverage of the affected area for the duration of the outbreak. Therefore, the area of outbreak was kept covered with the medical composition by reapplying as needed.

The four subjects were male. At the beginning of this study, their ages were 8, 17, 42 and 55. There were seven infectious outbreaks over approximately sixteen weeks. One of the outbreaks was HSV 2, genital herpes, four of the outbreaks were HSV 1 cold sores and two of the outbreaks were mouth ulcers. The 8, 42 and 55 year olds exhibited the HSV 1 (cold sores). The 55 year old also exhibited the HSV 2 (genital herpes). Both the 17 and 55 year old also had mouth ulcers. All subjects tested had a well established history of the disease and could identify the standard course of their disease. For each of the seven outbreaks, the antimicrobial compound (medicine) was applied directly on tissue at the prodrome stage or was applied directly on erupted vesicles or the ulcer. The antimicrobial compound was reapplied as necessary to maintain coverage.

Observations: With each application of the medicine, each individual (test subject) reported a loss of a tingling sensation within a few hours.

Results: The results of the with the medical treatment and medicine were unexpectedly good and very consistent. In each case, the subject happily reported that once the composition (medicine) was applied to the affected area, the pain completely stopped shortly thereafter. In the four cases, where the compound (medicine) was applied at the prodrome stage, the subjects reported that the pain stopped, all symptoms that would have previously escalated to full outbreak ceased and the outbreak never occurred. All external symptoms and physical manifestations of herpes disappeared within a few hours after the medicine was applied. In the two cases (HSV 1 & HSV 2), where the compound (medicine) was applied to erupted vesicles, the subject reported that the pain stopped within a three hours and the burning, itching and irritation resolved in six to ten hours and the vesicles dried up and scabbed over within twenty-four hours. In all cases, the other debilitating symptoms of malaise, inguinal swelling, weeping sores were resolved once the medicine was applied. In the two instances of mouth ulcers frequent hourly treatment with the formulation reduced swelling and burning sensations and the ulcers disappeared within two days.

In follow-up, where subjects had been given a supply of the composition (medicine) to test on future outbreaks, it was reported that if the initial signs of an outbreak exhibited, signaling the prodrome stage of an outbreak, the compound (medicine) was immediately applied by the subjects as per instructions and the outbreak was fully arrested and further symptoms never occurred. Significantly, it was also reported by one subject who was accustomed to experiencing several outbreaks annually had longer latency periods.

Example 2

A white male suffering from a yeast supra infection on his tongue due to radiation and chemotherapy was administered about 5 ml of a d-limonene formulation twice a day for about 30 days. The d-limonene formulation comprises 40% d-limonene in 60% Vitamin E oil as the carrier and was brushed on his tongue. After 30 days, no signs of yeast, which appeared as dark spots on his tongue, were observed.

The invention claimed is:

1. A method for killing or inhibiting the growth of herpes virus externally on the skin or within the mucosal cavity of a human, said method comprising administering a formulation comprising at least 10% by weight d-limonene to the human's skin, oral, or nasal cavity for a time sufficient to effectively eradicate or inhibit the growth of said herpes virus.

2. The method of claim wherein said d-limonene has a purity of at least 98.5% by weight.

3. The method of claim 1, wherein said herpes virus is herpes simplex virus 1.

4. The method of claim 1, wherein said herpes virus is herpes simplex virus 2.

5. The method of claim 1, wherein said formulation further comprises a carrier selected from the group consisting of glycerin, mineral oil, silica, cottonseed oil, coconut oil, vegetable oil, seed oil, fish oil, or animal oil, alcohol, talc, corn meal, beeswax, carnauba wax, beta carotene, garlic oil, camphor oil, soluble vitamins, Vitamin E oil, soluble minerals, rave seed oil, nut oils, olive oil, and liposomes.

6. The method of claim 1, wherein said carrier is Vitamin E oil.

7. The method of claim 1, wherein said carrier is camphor oil.

* * * * *

UNITED STATES PATENT AND TRADEMARK OFFICE
CERTIFICATE OF CORRECTION

| | |
|---|---|
| PATENT NO. | : 8,492,443 B2 |
| APPLICATION NO. | : 11/444037 |
| DATED | : July 23, 2013 |
| INVENTOR(S) | : Joe S. Wilkins, Jr. |

It is certified that error appears in the above-identified patent and that said Letters Patent is hereby corrected as shown below:

Delete the title page and substitute therefore with the attached title page showing the corrected number of claims in the patent.

In the Specification:

In Column 2, line 13, before "mouth ulcer" insert --A.--

In the Claims:

In Column 6, line 59 (i.e. Claim 5), change "rave" to "rape."

In Column 6, line 60 (i.e. Claim 6), change "1" to "5."

In Column 6, line 62 (i.e. Claim 7), change "1" to "5."

In Column 6, after line 63, insert the following claim:

--8. The method of claim 1, wherein said formulation comprises about 10% to about 50% d-limonene by weight.--

Signed and Sealed this
Fifth Day of November, 2013

Teresa Stanek Rea
*Deputy Director of the United States Patent and Trademark Office*

CERTIFICATE OF CORRECTION (continued)

(12) United States Patent
Wilkins, Jr.

(10) Patent No.: US 8,492,443 B2
(45) Date of Patent: Jul. 23, 2013

(54) TREATMENT FOR HERPES SIMPLEX VIRUS AND OTHER INFECTIOUS DISEASES

(76) Inventor: Joe S. Wilkins, Jr., Navasota, TX (US)

(*) Notice: Subject to any disclaimer, the term of this patent is extended or adjusted under 35 U.S.C. 154(b) by 1183 days.

(21) Appl. No.: 11/444,037

(22) Filed: May 31, 2006

(65) Prior Publication Data

US 2006/0217438 A1  Sep. 28, 2006

Related U.S. Application Data

(63) Continuation-in-part of application No. 10/615,589, filed on Jul. 8, 2003, now abandoned.

(60) Provisional application No. 60/394,333, filed on Jul. 8, 2002.

(51) Int. Cl.
*A01N 27/00* (2006.01)
*A61K 31/015* (2006.01)

(52) U.S. Cl.
USPC .................................................. 514/763

(58) Field of Classification Search
USPC .................................................. 514/763
See application file for complete search history.

(56) References Cited

U.S. PATENT DOCUMENTS

| | | | | |
|---|---|---|---|---|
| 3,023,144 A * | 2/1962 | Greathouse et al. | | 514/164 |
| 5,260,342 A * | 11/1993 | Herman | | 514/724 |
| 5,385,733 A * | 1/1995 | Mankovitz | | 424/771 |
| 5,894,019 A * | 4/1999 | Hesse et al. | | 424/484 |
| 5,900,416 A * | 5/1999 | Markson | | 424/728 |
| 6,077,862 A * | 6/2000 | Camden | | 514/388 |
| 6,419,936 B1 * | 7/2002 | Schmoyer | | 424/401 |
| 6,475,526 B1 * | 11/2002 | Smith | | 424/642 |
| 2002/0141959 A1 * | 10/2002 | Peterson et al. | | 424/70.12 |
| 2003/0104082 A1 | 6/2003 | Squires | | |

OTHER PUBLICATIONS

Bourne et al (Plant products as topical microbicide candidates: assessment of in vitro and in vivo activity against herpes simplex virus type 2, Antiviral Research, 42 (3) Jul. 1999, pp. 219-226).*
Sivropoulou et al (J. Agric. Food Chem. 1997, 45, 3197-3201).*
Herting and Drury (The Journal of Nutrition, 81(4) (1963) 335-342).*
Bourne et al (Antiviral Research, vol. 42, Iss 3, 1999, pp. 219-226).*
Australian office action for U.S. Appl. No. 10/615,589) (Jan. 7, 2008) (2 pages).

* cited by examiner

*Primary Examiner* — Benjamin Packard
(74) *Attorney, Agent, or Firm* — Laura G. Barrow

(57) ABSTRACT

Topical formulations and methods use are described herein for relieving symptoms created by herpes simplex, mouth ulcers, and yeast infections. The formulations comprise effective amounts of d-limonene.

8 Claims, No Drawings